US011555807B2

(12) United States Patent
Hasegawa

(10) Patent No.: US 11,555,807 B2
(45) Date of Patent: Jan. 17, 2023

(54) METHOD FOR MEASURING GLYCATED HEMOGLOBIN AND DEVICE FOR MEASURING GLYCATED HEMOGLOBIN

(71) Applicant: TOSOH CORPORATION, Shunan (JP)

(72) Inventor: Sachiyuki Hasegawa, Ayase (JP)

(73) Assignee: TOSOH CORPORATION, Shunan (JP)

(*) Notice: Subject to any disclaimer, the term of this patent is extended or adjusted under 35 U.S.C. 154(b) by 1106 days.

(21) Appl. No.: 16/099,766

(22) PCT Filed: Apr. 12, 2017

(86) PCT No.: PCT/JP2017/014984
§ 371 (c)(1),
(2) Date: Nov. 8, 2018

(87) PCT Pub. No.: WO2017/195522
PCT Pub. Date: Nov. 16, 2017

(65) Prior Publication Data
US 2019/0120803 A1 Apr. 25, 2019

(30) Foreign Application Priority Data
May 11, 2016 (JP) .............................. JP2016-095191

(51) Int. Cl.
G01N 33/72 (2006.01)
G01N 30/86 (2006.01)
G01N 30/88 (2006.01)
G01N 33/49 (2006.01)
G01N 30/02 (2006.01)
B01D 15/36 (2006.01)

(52) U.S. Cl.
CPC ......... G01N 30/8637 (2013.01); G01N 30/02 (2013.01); G01N 30/86 (2013.01); G01N 30/88 (2013.01); G01N 33/49 (2013.01); G01N 33/723 (2013.01); B01D 15/362 (2013.01); G01N 30/8631 (2013.01); G01N 30/8679 (2013.01); G01N 2030/8822 (2013.01)

(58) Field of Classification Search
CPC .......... G01N 2030/8822; G01N 30/02; G01N 30/86; G01N 30/8637; G01N 30/8624; G01N 30/8631; G01N 30/8641; G01N 30/8679; G01N 30/88; G01N 33/49; G01N 33/721; G01N 33/723; G01N 33/726; B01D 15/362
USPC ............ 702/19, 27, 32; 436/63, 66, 67, 161; 422/70
See application file for complete search history.

(56) References Cited

U.S. PATENT DOCUMENTS

| 5,417,853 A | 5/1995 | Mizuno et al. | |
|---|---|---|---|
| 2012/0017706 A1* | 1/2012 | Yoshida | G01N 30/8651 73/866.3 |
| 2013/0199277 A1 | 8/2013 | Taira et al. | |
| 2014/0162369 A1* | 6/2014 | Oishi | B01J 20/285 436/66 |
| 2014/0238113 A1* | 8/2014 | Oishi | G01N 30/14 73/61.56 |
| 2015/0204889 A1* | 7/2015 | Taira | G01N 30/88 436/66 |

FOREIGN PATENT DOCUMENTS

| JP | 5-5730 A | 1/1993 |
|---|---|---|
| JP | 09-264889 A | 10/1997 |
| JP | 2001-221788 A | 8/2001 |
| JP | 4740036 B2 | 8/2011 |
| JP | 5013560 B2 | 8/2012 |
| JP | 2012-215470 A | 11/2012 |
| JP | 2017-194349 A | 10/2017 |
| WO | 00/08460 * | 2/2000 |

OTHER PUBLICATIONS

International Preliminary Report on Patentability with a Translation of Written Opinion issued from the International Bureau in counterpart International Application No. PCT/JP2017/014984, dated Nov. 13, 2018.
Randie R. Little, Ph.D., et al., "A Review of Variant Hemoglobins Interfering with Hemoglobin A1c Measurement," Journal of Diabetes Science and Technology, May 2009, pp. 446-451, vol. 3, No. 3.
Randie R. Little et al., "Effects of Hemoglobin (Hb) E and HbD Traits on Measurements of Glycated Hb ($HbA_{1c}$) by 23 Methods," Clinical Chemistry, 2008, pp. 1277-1282, vol. 54, No. 8.
Lynn Bry et al., "Effects of Hemoglobin Variants and Chemically Modified Derivatives on Assays for Glycohemoglobin," Clinical Chemistry, 2001, pp. 153-163, vol. 47, No. 2.
"HbA1c and interference due to hemoglobin disorders," Scientific discussion paper, Roche Diagnostics International Ltd., 2013, 16 pages.
Bushra Moiz et al., "Performance evaluation of ion exchange and affinity chromatography for $HbA_{1c}$ estimation in diabetic patients with HbD: A study of 129 samples," Clinical Biochemistry, 2008, pp. 1204-1210, vol. 41.

(Continued)

Primary Examiner — Maureen Wallenhorst
(74) Attorney, Agent, or Firm — Sughrue Mion, PLLC

(57) ABSTRACT

A method for measuring a proportion of sA1c (%), which includes, when a peak derived from abnormal hemoglobin D, abnormal hemoglobin S or abnormal hemoglobin C is identified, calculation of the peak area, and measurement of the proportion of sA1c (%) corrected by using the calculation results. Results of measurement are obtained, by cation exchange chromatography, of sA1c (%) with a subject who provided a blood sample containing abnormal hemoglobin D, abnormal hemoglobin S or abnormal hemoglobin C by eliminating influences by such abnormal hemoglobin.

1 Claim, 6 Drawing Sheets

(56) References Cited

OTHER PUBLICATIONS

Sharon Saw et al., "Identification of hemoglobin variants in samples received for glycated hemoglobin testing," Clinica Chimica Acta, 2013, pp. 173-175, vol. 415.

International Search Report of PCT/JP2017/014984 dated Jul. 11, 2017.

* cited by examiner

Cation exchange chromatography device

11 A means of sample injection
12 A means of liquid transportation
13 A means of separation
14 A means of detection
15 A means of analysis
16 Baseline setting module
17 Peak identification module
18 Peak area calculation module
19 sA1c proportion calculation module
20 A means of output

METHOD FOR MEASURING GLYCATED HEMOGLOBIN AND DEVICE FOR MEASURING GLYCATED HEMOGLOBIN

CROSS REFERENCE TO RELATED APPLICATIONS

This application is a National Stage of International Application No. PCT/JP2017/014984 filed Apr. 12, 2017, claiming priority based on Japanese Patent Application No. 2016-095191 filed May 11, 2016.

TECHNICAL FIELD

The present invention relates to a method and a device for measuring glycated hemoglobin in a blood sample by liquid chromatography. Particularly, it relates to a method and a device for measuring glycated hemoglobin, capable of measuring glycated hemoglobin used as an index of diabetes diagnosis with respect to a blood sample group which may include a blood sample containing abnormal hemoglobin.

BACKGROUND ART

Hemoglobin comprises hemoglobin A having an $\alpha 2\beta 2$ structure consisting of two $\alpha$ chains and two $\beta$ chains, constituting about 97% of total hemoglobin, and hemoglobin F having an $\alpha 2\gamma 2$ structure consisting of two $\alpha$ chains and two $\gamma$ chains, constituting less than 1% of total hemoglobin, and hemoglobin A2 having an $\alpha 2\delta 2$ structure consisting of two $\alpha$ chains and two $\delta$ chains, constituting less than 1% of total hemoglobin, as well.

Hemoglobin forms glycated hemoglobin by non-enzymatic glycation with sugar (plasma glucose) or its metabolite present in blood. Hemoglobin A1 formed by glycation of hemoglobin A constituting the most part of total hemoglobin, does not strictly constitute the entire glycated hemoglobin, but is clinically considered synonymously with glycated hemoglobin in many cases. Hemoglobin A1 is further separated into A1a, A1b and A1c. The proportion of so-called stable hemoglobin A1c (hereinafter sometimes abbreviated as "sA1c"), the concentration of which changes reflecting a change of the blood glucose level in the past two to three months, not being influenced by a temporary increase of the blood glucose level e.g. by a diet, to total hemoglobin (hereinafter sometimes abbreviated as A1c %) is widely employed as an index of diabetes diagnosis or follow-up of diabetes patients.

Measurement of glycated hemoglobin has been conducted by means of liquid chromatography. Measurement of glycated hemoglobin by liquid chromatography is roughly classified into measurement by cation exchange chromatography by which hemoglobin is separated into various hemoglobin components utilizing a difference in charge of them using a packing material to which an ion exchange substance is fixed, and measurement by affinity chromatography using a packing material to which aminophenylboronic acid groups having high affinity for sugar are fixed. By affinity chromatography, which utilizes affinity for the sugar chain moiety, various glycated hemoglobin components including sA1c are to be measured (Non-Patent Document 2), and in this case also, the proportion of glycated hemoglobin to total hemoglobin is utilized. On the other hand, by cation exchange chromatography, various hemoglobin components are separated, and only sA1c is measured, whereupon the proportion A1c % to total hemoglobin is calculated.

Hemoglobin also includes various abnormal hemoglobin components such as hemoglobin E, hemoglobin D, hemoglobin S and hemoglobin C caused by hemoglobin gene mutations. And in recent years, reports have been published that in rare cases, if a blood sample to be subjected to glycated hemoglobin measurement contains various abnormal hemoglobin components caused by such gene mutations, by measurement by affinity chromatography, measurement results reflecting symptoms of a subject who provided the blood sample can be obtained, whereas by measurement by cation chromatography, the sA1c % measurement value is low and in some cases, hardly reflects symptoms of a subject who provided the blood sample (Non-Patent Documents 1 to 3).

PRIOR ART DOCUMENTS

Patent Documents

Patent Document 1: JP-A-H09-264889

Non-Patent Documents

Non-Patent Document 1: R. R. Little and W. L. Roberts, J Diabetes Sci Technol, Vol 3 (3), 446-451 (2009).
Non-Patent Document 2: R. R. Little et al., Clin Chem, Vol 54 (8), 1277-1282 (2008).
Non-Patent Document 3: L. Bry et al., Clin Chem, Vol 47 (2), 153-163 (2001).

DISCLOSURE OF INVENTION

Technical Problem

In a case where a blood sample to be measured contains abnormal hemoglobin D, abnormal hemoglobin S or abnormal hemoglobin C, when sA1c is measured by cation exchange chromatography, a part of such abnormal hemoglobin components are eluted at the same time or after A0 which is a non-glycated component of hemoglobin A. In such a case, even when a remarkable peak corresponding thereto is excluded from calculation of A1c %, A1c % shows a low value, whereas by measurement of glycated hemoglobin by affinity chromatography, it was confirmed that the value of glycated hemoglobin to total hemoglobin is not influenced. Under these circumstances, the present invention is to obtain a measurement result of A1c % reflecting symptoms of a subject who provided the blood sample, excluding influences by abnormal hemoglobin D, abnormal hemoglobin S or abnormal hemoglobin C of which there are many carriers globally, when the blood sample contains such an abnormal hemoglobin.

Solution to Problem

The present inventor has obtained a chromatogram by subjecting a blood sample containing abnormal hemoglobin D, abnormal hemoglobin S or abnormal hemoglobin C to cation exchange chromatography and analyzed the chromatogram and as a result, found that a peak which is not confirmed in a chromatogram of a healthy subject, appears. He has further found that the A1c % corrected based on the areas of such peaks highly correlates with the measurement results by affinity chromatography which are considered to be hardly influenced by abnormal hemoglobin D, abnormal hemoglobin S or abnormal hemoglobin C, and accomplished the present invention.

That is, the present invention has been accomplished as a result of extensive studies to achieve the above objects.

[1] A method for measuring stable glycated hemoglobin sA1c, which comprises (1) a step of subjecting a blood sample after hemolysis to cation exchange chromatography to elute sA1c as separated from other hemoglobin components thereby to obtain a chromatogram showing elution of hemoglobin fractions, (2) a step of identifying a sA1c peak in the obtained chromatogram and calculating its peak area, (3) a step of identifying peaks of hemoglobin components other than sA1c in the obtained chromatogram and calculating their peak areas, (4) a step of calculating the proportion (%) of the sA1c peak area to the total hemoglobin peak area, (5) a step of identifying a non-glycated peak of abnormal hemoglobin D, abnormal hemoglobin S or abnormal hemoglobin C from peaks which appear after a non-glycated peak of hemoglobin A, and (6) a step of estimating the area of a glycated peak of abnormal hemoglobin D, abnormal hemoglobin S or abnormal hemoglobin C based on a non-glycated peak area and the like of the abnormal hemoglobin identified, wherein the proportion (%) of the sA1c peak area in the above step 4 is corrected based on the estimated calculation results.

[2] The method according to [1], wherein when a peak of abnormal hemoglobin D or abnormal hemoglobin S is identified in the step 5, the proportion (%) of the sA1c peak area to the total peak area of hemoglobin A is corrected on the assumption that the glycated peak of the abnormal hemoglobin D or abnormal hemoglobin S appears as overlapping the non-glycated peak A0 of hemoglobin A and that the proportion of the sA1c peak area to the total peak areas of hemoglobin A is equal to the proportion of the glycated peak area of the abnormal hemoglobin to the sum of the other peak areas of the abnormal hemoglobin.

[3] The method according to [1], wherein when a peak of abnormal hemoglobin C is identified in the step 5, the proportion (%) of the sA1c peak area to the total peak area of hemoglobin A is corrected on the assumption that the glycated peak of the abnormal hemoglobin C appears after the non-glycated peak A0 of hemoglobin A.

[4] The method according to [1] or [2], wherein when a peak of abnormal hemoglobin D or abnormal hemoglobin S is identified in the step 5, the proportion (%) of the sA1c peak area to the total peak area of hemoglobin A is corrected in accordance with the following formulae, on the assumption that the glycated peak of the abnormal hemoglobin D or abnormal hemoglobin S appears as overlapping the non-glycated peak A0 of hemoglobin A and that the proportion of the sA1c peak area to the total peak area of hemoglobin A is equal to the proportion of the glycated peak area of the abnormal hemoglobin to the sum of the other peak areas of the abnormal hemoglobin:

$$A1c\ \%=100sA1c/(A0+\alpha)=100X1c/(X0+\beta+X1c)$$

$$A'=A0+X1c$$

$$X1c=[(A'+\alpha-sA1c)$$

$$-\sqrt{\{(A+\alpha-sA1c)^2-4sA1c(X0+\beta)\}}]/2$$

wherein A' is the sum of A0 and a glycated peak area of abnormal hemoglobin which coelutes with A0 and is an area of the peak observed as A0 on the chromatogram, sA1c and A0 are respectively glycated and non-glycated peak areas of hemoglobin A, X1c and X0 are respectively a glycated peak area of abnormal hemoglobin which coelutes with A0 and a non-glycated peak area of abnormal hemoglobin which appears after A0, $\alpha$=A1a+A1b+LA1c+sA1c, and $\beta$ is one obtained by subtracting X0 from the total area of peaks which appear after A0.

[5] The method according to [1] or [3], wherein when a peak of abnormal hemoglobin C is identified in the step 5, the proportion (%) of the sA1c peak area to the total peak area of hemoglobin A is corrected in accordance with the following formula, on the assumption that the glycated peak of the abnormal hemoglobin C appears after the non-glycated peak A0 of hemoglobin A:

$$A1c\ \%=100sA1c/(A'+\alpha)$$

wherein A' is the peak area observed as A0 on the chromatogram, sA1c and A0 are respectively glycated and non-glycated peak areas of hemoglobin A, and $\alpha$=A1a+A1b+LA1c+sA1c.

[6] A device for measuring stable glycated hemoglobin sA1c, comprising:

(1) a means of sample injection for injecting a hemolyzed blood sample, (2) a means of separation comprising a resin having cation exchange capacity, (3) a means of liquid transportation for transporting liquids, (4) a means of detection for detecting hemoglobin eluted from the means of separation and obtaining a chromatogram, and (5) a means of analysis for analyzing the chromatogram detected by the means of detection, wherein the means of analysis is a) to set a baseline to calculate peak areas which appear in the chromatogram, b) to identify the type of hemoglobin from which the peak that appears in the chromatogram is derived, c) to calculate the peak area which appears in the chromatogram, and d) to calculate the proportion (%) of the sA1c peak area to the total hemoglobin peak area, and when a peak of abnormal hemoglobin D, abnormal hemoglobin S or abnormal hemoglobin C is identified in the above b, the peak area of the abnormal hemoglobin is calculated, the proportion (%) of the sA1c peak area is corrected in the above d based on the calculation results, and the proportion (%) of the corrected sA1c peak area is measured.

[7] The measurement device according to [6], wherein the most remarkable peak which appears after the non-glycated peak of hemoglobin A is identified as a peak of abnormal hemoglobin D, abnormal hemoglobin S or abnormal hemoglobin C, and the analysis is conducted in the means of analysis.

[8] The measurement device according to [6] or [7], wherein when a peak of abnormal hemoglobin D or abnormal hemoglobin S is identified in the above b, the proportion (%) of the sA1c peak area is corrected in the above d on the assumption that the glycated peak of the abnormal hemoglobin D or abnormal hemoglobin S appears as overlapping the non-glycated peak A0 of hemoglobin A and that the proportion of the sA1c peak area to the total peak area of hemoglobin A is equal to the proportion of the glycated peak area of the abnormal hemoglobin to the sum of the other peak areas of the abnormal hemoglobin.

[9] The measurement device according to [6] or [7], wherein when a peak of abnormal hemoglobin C is identified in the above b, the proportion (%) of the sA1c peak area is corrected in the above d on the assumption that the glycated peak of the abnormal hemoglobin C appears after the non-glycated peak A0 of hemoglobin A.

Now, the present invention will be described in detail below. Under conditions described in the after-mentioned Examples, when blood samples containing each of abnormal hemoglobin D, abnormal hemoglobin S and abnormal hemoglobin C are subjected to cation exchange chromatography, chromatograms shown in FIGS. 5, 6 and 7 are obtained, respectively. By comparison between such chromatograms and a chromatogram (FIG. 4) obtained by subjecting a blood sample of a healthy subject to cation chromatography, remarkable peaks (H-V0, H-V1 and H-V2) corresponding to the respective abnormal hemoglobin components appear after the peak (A0) of non-glycated hemoglobin A.

Further, in the present invention, H-V0, H-V1 and H-V2 indicate remarkable peaks other than hemoglobin A of which the identification and elution times are set by the compositions of the elution buffers and their flow rates in the chromatogram. Such H-V0, H-V1 and H-V2 peaks are estimated to be non-glycated peaks derived from the respective abnormal hemoglobin components, and the glycated peaks of the respective abnormal hemoglobin components are estimated to coelute with A0.

Accordingly, in the present invention, it was found that A1c % relating to hemoglobin A can be corrected when an abnormal hemoglobin specimen is measured on the following assumption with respect to the proportion of a peak area which coelutes with A0 and is considered to be derived from abnormal hemoglobin, that is, the peak area of glycated abnormal hemoglobin which coelutes with A0, to the areas of peaks which appear after A0 and are considered to be derived from the abnormal hemoglobin, including the remarkable non-glycated peak (H-V0, H-V1 or H-V2) of the abnormal hemoglobin.

The present invention is characterized in that A1c % is corrected on the assumption that the proportion of the glycated peak sA1c relating to hemoglobin A to the sum of A1a, A1b, LA1c and sA1c derived from hemoglobin A including A0, is the same as that in the case of abnormal hemoglobin. Specifically, in order to solve the problem that the glycated peak of abnormal hemoglobin coeluted with A0 cannot be isolated on the chromatogram, on the above assumption, X1c and A0 are estimated by $$X1c=[(A'+\alpha-sA1c)-\sqrt{\{(A'+\alpha-sA1c)^2-4sA1c(X0+13)\}}]/2 \quad \text{formula (3)}$$

which satisfies $$A1c\%=100sA1c/(A0+\alpha)=100X1c/(X0+\beta+X1c) \quad \text{formula (1)}$$

$$A'=A0+X1c \quad \text{formula (2),}$$

and A1c % corrected from $100sA1c/(A0+\alpha)$ of the formula (1) is calculated, whereby the above object can be achieved.

Here, A' is the sum of A0 and a glycated peak area of abnormal hemoglobin which coelutes with A0. A0 and the glycated peak of abnormal hemoglobin which coelutes with A0 cannot be separated on the chromatogram and are measured as a whole. sA1c and A0 respectively represent glycated and non-glycated peak areas of hemoglobin A, and X1c and X0 respectively represent a glycated peak area of abnormal hemoglobin which coelutes with A0 and a non-glycated peak area of abnormal hemoglobin which appears after A0. Further, $\alpha=A1a+A1b+LA1c+sA1c$, and $\beta$ is one obtained by subtracting X0 from the total area of peaks which appear after A0.

Here, in a case where the H-V2 peak, that is, abnormal hemoglobin C is detected as abnormal hemoglobin, its glycated peak is highly likely to appear after A0, and accordingly the assumption of the formula (2) cannot be applied. Corrected A1c % is calculated from $$A1c\%=100sA1c/(A'+\alpha) \quad \text{formula (4)}$$

assigning A0=A' to the formula (1), whereby the above object can be achieved.

Further, according to the present invention, the proportion of the abnormal hemoglobin glycated peak to the sum of the areas of peaks which appear after A0 and are considered to be derived from abnormal hemoglobin, that is, a remarkable non-glycated peak (H-V0, H-V1 or H-V2) of abnormal hemoglobin and the abnormal hemoglobin glycated peak which coelutes with A0, is calculated in accordance with the above formula, even when the abnormal hemoglobin is other than abnormal hemoglobin D, abnormal hemoglobin S and abnormal hemoglobin C.

The measurement method of the present invention can be easily conducted by an automated measurement device, for example, a device comprising (1) a means of sample injection for injecting a hemolyzed blood sample, (2) a means of separation comprising a resin having cation exchange capacity, (3) a means of liquid transportation for transporting liquids, (4) a means of detection for detecting hemoglobin eluted from the means of separation and obtaining a chromatogram, and (5) a means of analysis for analyzing the chromatogram detected by the means of detection. The present invention further relates to a program for measuring stable glycated hemoglobin sA1c to make the above means (1) to (5) executed by a computer.

The means of sample injection (1) is to inject a certain amount of a blood sample to the after-described means of separation, and may be constituted using a commercial autosampler, a six-way valve and so on. Measurement of sA1c is conducted by using a hemolyzed blood sample, and a hemolysis operation may be carried out in the means of sample injection, or a blood sample after subjected to hemolysis may be subjected to the means of sample injection. Hemolysis may be carried out e.g. by adding a blood sample containing blood cell components to a hypertonic solution.

The means of separation (2) comprising a resin having cation exchange capacity, may, for example, be a column packed with a resin having modification groups bonded thereto for so-called cation exchange chromatography, for example, a sulfonic type.

The resin for cation exchange chromatography may, for example, be a non-porous cation exchanger, and a column packed with such a resin may, for example, be non-porous cation exchange column TSKgel (registered trademark) SP-NPR manufactured by TOSOH CORPORATION.

The means of liquid transportation (3) for transporting liquids is to transport a blood sample injected from the means of sample injection or elution buffers to make hemoglobin be eluted to the means of separation and may, for example, be a pump.

As the elution buffers, various elution buffers have been used, and for example, a mixer for gradient elution utilizing three types of elution buffers with different salt concentrations may be provided.

The means of detection (4) for detecting hemoglobin eluted from the means of separation and obtaining a chromatogram is not particularly limited so long as it can detect hemoglobin, and may, for example, be an absorption detector capable of detecting elution of hemoglobin as a protein based on an absorbance at 415 nm or an electric conductivity detector.

The means of analysis (5) is a means for analyzing the chromatogram detected by the means of detection, and the measurement device of the present invention is characterized by this means of analysis. The means of analysis first sets a baseline to calculate peak areas which appear in the chromatogram. To set a baseline, various methods have been proposed (for example, Patent Document 1), but the method is not particularly limited. Subsequently to setting of a baseline, the type of hemoglobin from which the peak that appears in the chromatogram is derived is identified. For the identification, the device is provided with a means of storage to store the elution time expected for each type of hemoglobin thereby to identify each peak from the elution time. The setting of a baseline and the peak identification may be conducted in reverse order. Each peak area which appears in the chromatogram is calculated in such a manner, and then the proportion (%) of the sA1c peak area to the total hemoglobin peak area is obtained, and in a case where a peak corresponding to abnormal hemoglobin D or abnormal hemoglobin S, that is, H-V0 or H-V1 is identified at the time of the peak identification, the total peak area (Total area) in the chromatogram and the respective peak areas of A1a, A1b, HbF, LA1c, sA1c, A' and H-V0 or H-V1 are calculated, the X1c area and the A0 area are defined by the formulae (3) and (2), respectively, and A1c % is calculated by the formula (1).

Further, in a case where a peak corresponding to abnormal hemoglobin C, that is, H-V2 is identified at the time of the peak identification, the respective peak areas of A1a, A1b, HbF, LA1c, sA1c, A' and H-V2 are calculated, and A1c % is calculated from the formula (4). On that occasion, the denominator of the formula (4) may be calculated by Total area-X0-$\beta$-HbF from the peak areas, that is, total area, X0 and 3.

The means of analysis is not particularly limited so long as the chromatogram detected by the means of detection can be analyzed as above, and may be constituted, for example, by installing a program for the above analysis in a computer provided with a processor. Such a computer may be integrated into the device of the present invention, or may be a so-called external computer.

The measurement device of the present invention will be described in further detail with reference to FIG. 11. A hemolyzed blood sample introduced into a means of sample injection 11 is transported to a means of separation 13, and further elution buffers are transported to the means of separation 13 by a means of liquid transportation 12, whereby hemoglobin is separated into fractions and eluted. The eluted hemoglobin is detected by a means of detection 14 to give a chromatogram, and the obtained chromatogram is analyzed by a means of analysis 15. The means of analysis 15 comprises a baseline setting module 16, a peak identification module 17, a peak area calculation module 18 and a sA1c proportion calculation module 19, and first, the baseline setting module 16 sets a baseline to calculate peak areas which appear in the chromatogram.

Then, the peak identification module 17 identifies the type of hemoglobin from which the peak that appears in the chromatogram is derived. The peak identification module 17 can judge presence or absence of peaks (H-V0, H-V1 and H-V2) derived from abnormal hemoglobin D, abnormal hemoglobin S and abnormal hemoglobin C, by comparing a chromatogram of a blood sample containing no abnormal hemoglobin D, S and C stored in a means of storage, and a chromatogram provided by the means of detection 14. As another specification method, for example, first elution times of peaks derived from abnormal hemoglobin obtained from a chromatogram of a blood sample containing abnormal hemoglobin D, S or C, are stored in a means of storage, and whether a peak corresponding to one of the elution times appears in the chromatogram is judged, and if the peak appears, the peak is identified as one of the peaks (H-V0, H-V1 or H-V2) derived from abnormal hemoglobin D, S or C. Then, the peak area calculation module 18 calculates the peak area of each hemoglobin component.

Finally, the sA1c proportion calculation module 19 determines the proportion (%) of the sA1c peak area to the total hemoglobin peak area, that is, A1c %. Here, if the peak identification module 17 identifies a peak derived from abnormal hemoglobin D, S or C, the sA1c proportion calculation module 19 corrects A1c % which is the characteristic of the present invention. If no peak derived from abnormal hemoglobin D, S or C is identified by the peak identification module 17, of course, the A1c % proportion calculation module 19 calculates A1c % without correction with respect to A1c %. Specifically, when the peak identification module 17 judges that H-V0 or H-V1 is present, the total peak area (Total area) and the respective peak areas of A1a, A1b, HbF, LA1c, sA1c, A' and H-V0 or H-V1 in the chromatogram are calculated, the X1c area is obtained from the formula (3), the A0 area is determined by the formula (2), and A1c % is calculated from the formula (1). On the other hand, when the peak identification module 17 judges that H-V2 is present, the respective peak areas of A1a, A1b, HbF, LA1c, sA1c, A' and H-V2 are calculated, and A1c % is calculated from the formula (4), or, the Total area and the respective peak areas of X0, P and HbF are calculated, the denominator of the formula (4) is calculated by Total area-X0-$\beta$-HbF, and A1c % is calculated.

The above-calculated A1c % is further calibrated and corrected by means of calibration using a reference material specified by each academic society such as National Glycohemoglobin Standardization Program (NGSP), International Federation of Clinical Chemistry and Laboratory Medicine (IFCC) or The Japan Diabetes Society (JDS) to calculate A1c % as an index to carry out e.g. diagnosis in accordance with the standard specified by the academic society, and further, good correlation with measurement results by affinity chromatography can be achieved by excluding the influence by abnormal hemoglobin D, S and C. The results analyzed by the means of analysis 15 may be displayed or printed by a means of output 20. The present invention also relates to a program for measuring stable glycated hemoglobin sA1c which makes each module in the means of analysis executed by a computer.

FIG. 12 is a diagram illustrating the means of analysis 15 in terms of the hardware constitution. The means of analysis 15 comprises a processor 21, a memory 22, an output interface 23, a means of auxiliary storage 24, an input interface 25, a means of input 26, etc. The processor 21 executes a program installed in the means of auxiliary storage 24, thereby to execute processing to realize the function which the means of analysis 15 fulfills. The memory 22 stores the program during the execution by the processor 21 and data temporarily used by the program. The memory 22 may have a read only memory (ROM) or a random access memory (RAM). The above 21 to 26 are electrically connected by a data bus 27. The output interface 23 is an interface circuit which outputs the chromatogram and the proportion (%) of sA1c calculated to a means of output such as a monitor or a printer. The input interface 25 is an interface circuit which inputs the chromatogram output from the means of detection. The means of input 26 is to receive operation input by a user, and is equipped with a conventional input device such as a keyboard, so as to start and shut down the device and to input e.g. information regarding the blood sample. These means are electrically connected by a bus.

In a case where the measurement device of the present invention comprises the above-exemplified means of display such as a monitor or a printer, if a peak derived from abnormal hemoglobin D, S or C (H-V0, H-V1 or H-V2) is identified, attention may be attracted by indicating that the peak is identified by such a means of display. Further, the measurement device of the present invention may further be such constituted that the means of display indicates the measurement results (A1c %) relating to the blood sample in which H-V0, H-V1 or H-V2 is identified and that the present invention is applied.

Advantageous Effects of Invention

In a case where a blood sample to be measured contains abnormal hemoglobin D, abnormal hemoglobin S or abnormal hemoglobin C, it is reported that when sA1c is measured by cation exchange chromatography, the sA1c value to total hemoglobin shows a low value even by calculation excluding a remarkable peak derived from the abnormal hemoglobin D, abnormal hemoglobin S or abnormal hemoglobin C, however, according to the present invention, influences by abnormal hemoglobin D, abnormal hemoglobin S and abnormal hemoglobin C are eliminated, and it is possible to obtain A1c % measurement results which reflect symptoms of a subject who provided the blood sample, and which are well correlated with measurement results by affinity chromatography which is reported to be hardly influenced by such abnormal hemoglobin.

DESCRIPTION OF EMBODIMENTS

Figure 1:
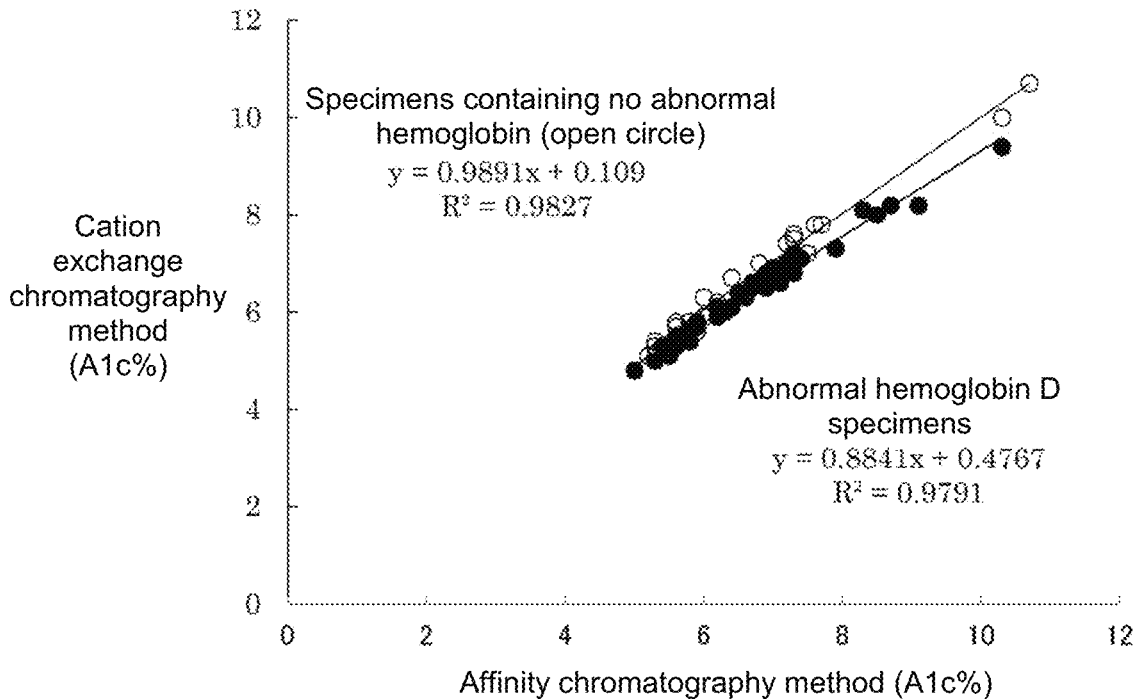
FIG. 1 is a diagram illustrating the correlation between measurement results by affinity chromatography and measurement results by cation exchange chromatography, with respect to blood samples containing abnormal hemoglobin D and blood samples containing no abnormal hemoglobin D.
Figure 2:
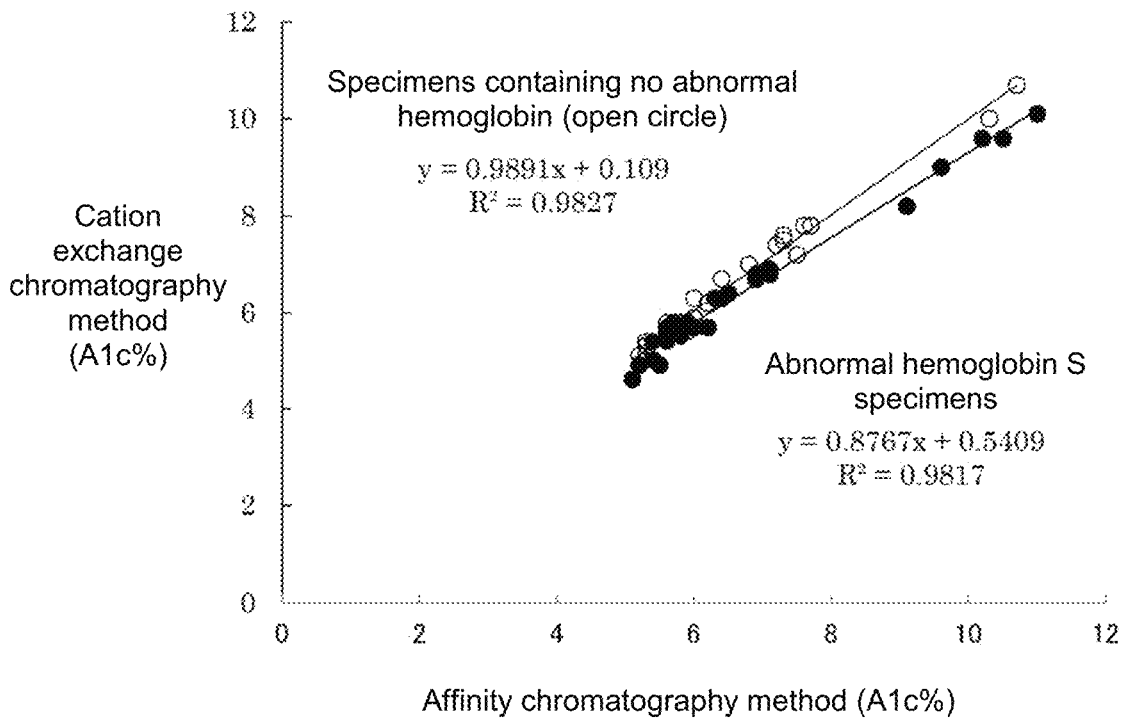
FIG. 2 is a diagram illustrating the correlation between measurement results by affinity chromatography and measurement results by cation exchange chromatography, with respect to blood samples containing abnormal hemoglobin S and blood samples containing no abnormal hemoglobin S.
Figure 3:
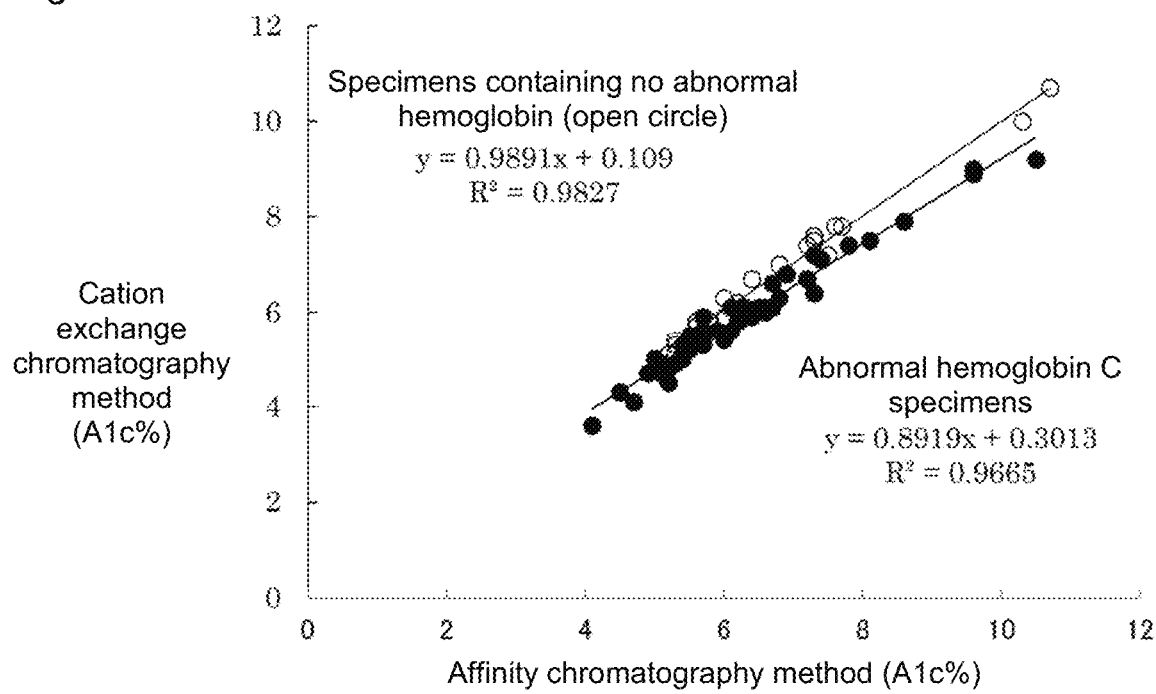
FIG. 3 is a diagram illustrating the correlation between measurement results by affinity chromatography and measurement results by cation exchange chromatography, with respect to blood samples containing abnormal hemoglobin C and blood samples containing no abnormal hemoglobin C.

FIGS. 1, 2 and 3 are diagrams illustrating the correlation between measurement results by affinity chromatography and measurement results by cation exchange chromatography, with respect to blood samples containing abnormal hemoglobin D, abnormal hemoglobin S or abnormal hemoglobin C (38, 33 or 53 samples respectively) and blood samples containing no such abnormal hemoglobin (22 samples, open circle).

The former samples were confirmed to contain abnormal hemoglobin D, abnormal hemoglobin S or abnormal hemoglobin C by a commercial apparatus (Capillarys 2 manufactured by Sebia).

Measurement by affinity chromatography is carried out by a commercial apparatus (Ultra$^2$ manufactured by Trinity Biotech), and measurement by cation chromatography is carried out by cation exchange chromatography using an Automated Glycohemoglobin Analyzer HLC-723G8 (tradename) manufactured by TOSOH CORPORATION equipped with a non-porous cation exchange column.

The vertical axis of FIGS. 1, 2 and 3 indicates measurement results by cation exchange chromatography, and the horizontal axis indicates measurement results by affinity chromatography, and all the results are the proportion (%) of sA1c to total hemoglobin, and all the results are obtained by plotting measurement results output from the device with dedicated reagents after calibration.

With respect to blood samples containing no abnormal hemoglobin (22 samples, open circle), there is a good correlation between results by affinity chromatography and results by cation exchange chromatography, however, with respect to blood samples containing abnormal hemoglobin D, abnormal hemoglobin S or abnormal hemoglobin C (38, 33 or 53 samples, filled circle), the results by cation exchange chromatography show lower values than the results by affinity chromatography.

Figure 4:
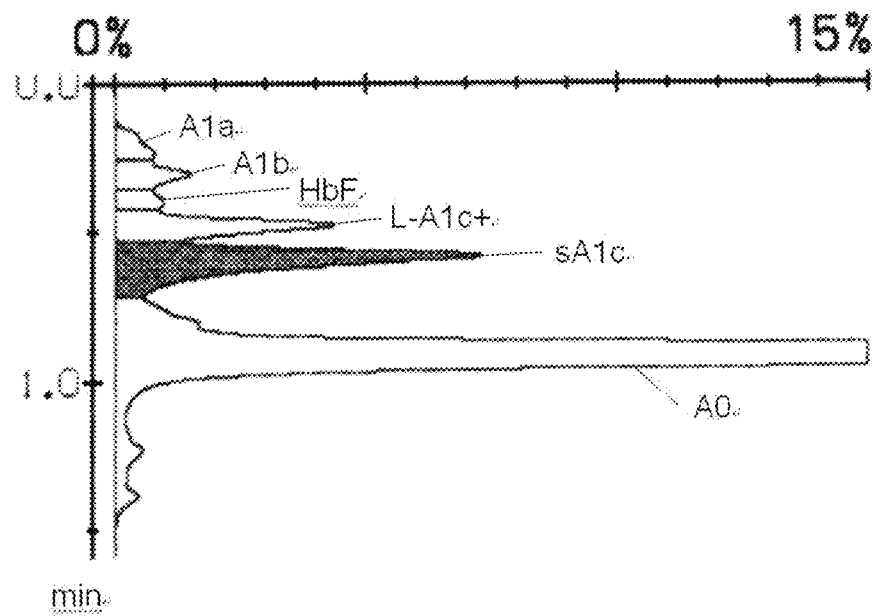
FIG. 4 is a chromatogram obtained by cation exchange chromatography with respect to a blood sample containing no abnormal hemoglobin D, abnormal hemoglobin S or abnormal hemoglobin C.
Figure 5:
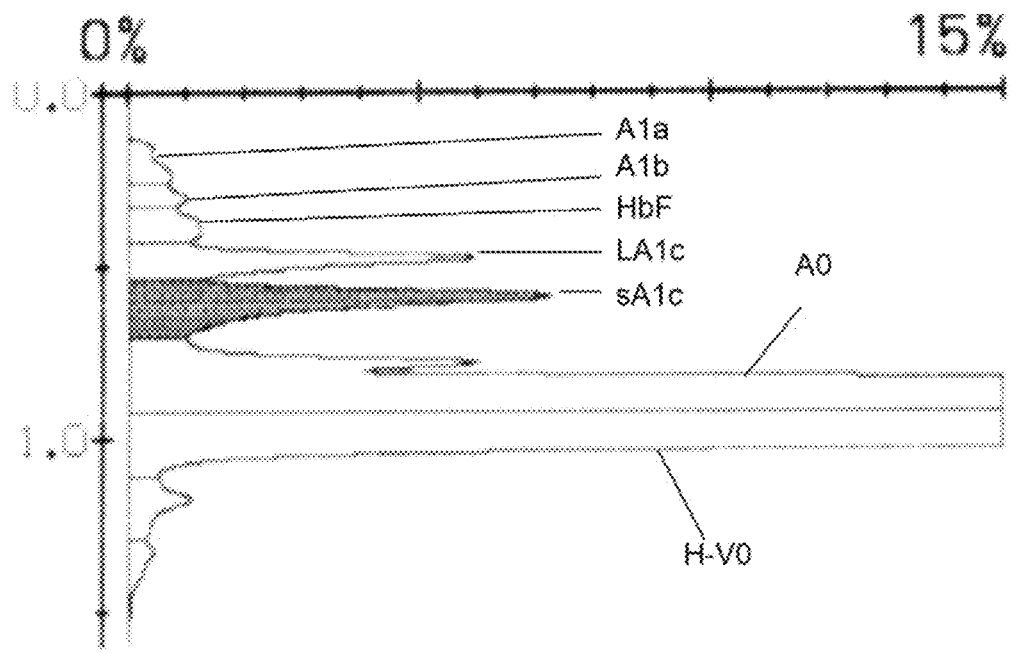
FIG. 5 is a chromatogram obtained by cation exchange chromatography with respect to a blood sample containing abnormal hemoglobin D.
Figure 6:
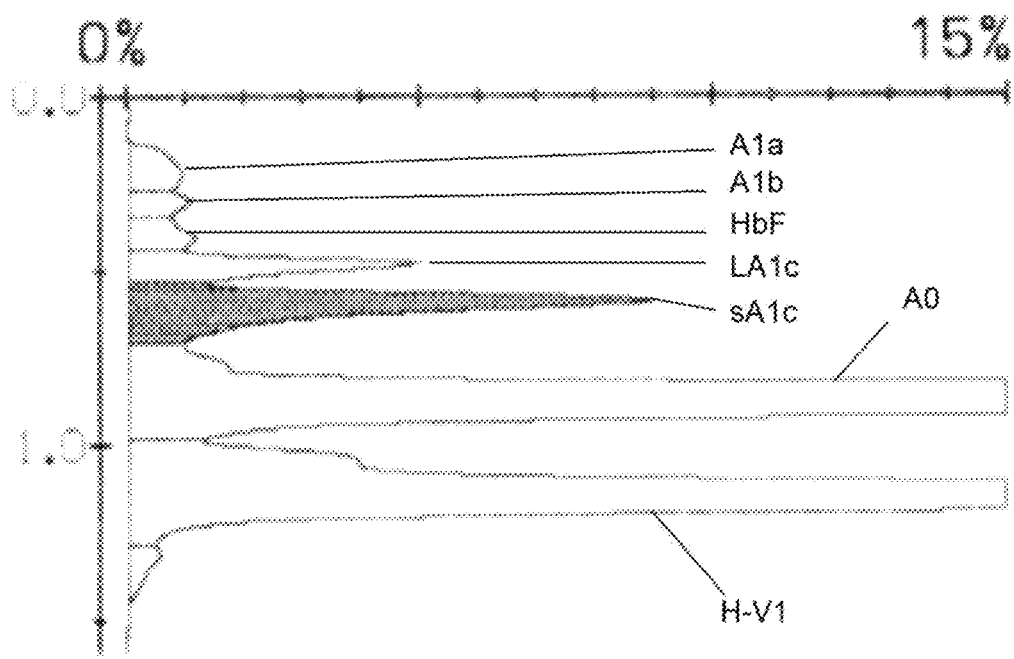
FIG. 6 is a chromatogram obtained by cation exchange chromatography with respect to a blood sample containing abnormal hemoglobin S.
Figure 7:
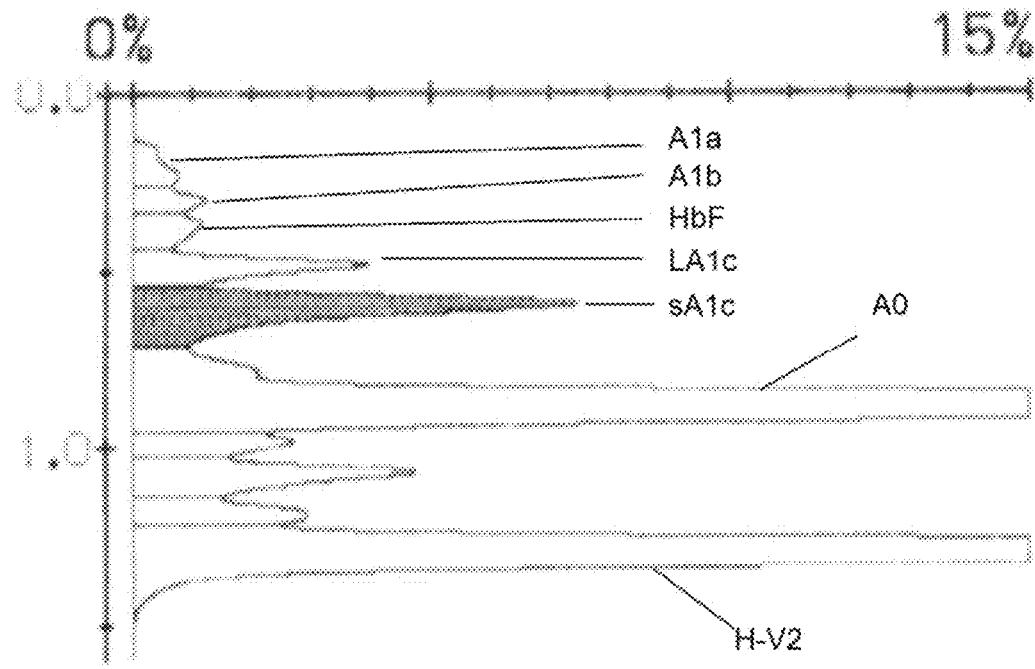
FIG. 7 is a chromatogram obtained by cation exchange chromatography with respect to a blood sample containing abnormal hemoglobin C.

FIG. 4 is an example of a chromatogram obtained by subjecting a blood sample of a healthy subject to cation exchange chromatography. With a blood sample from a healthy subject, no remarkable peak derived from other component appears after the hemoglobin A peak (A0). FIGS. 5, 6 and 7 are examples of chromatograms obtained by subjecting blood samples from subjects containing abnormal hemoglobin D, abnormal hemoglobin S or abnormal hemoglobin C, to cation exchange chromatography. As evident from FIGS. 5, 6 and 7, with the blood samples containing abnormal hemoglobin D, abnormal hemoglobin S or abnormal hemoglobin C, a remarkable peak (H-V0, H-V1 or H-V2) derived from such abnormal hemoglobin, which is not observed in FIG. 4, appears after the hemoglobin A peak (A0).

Accordingly, peaks derived from abnormal hemoglobin D, abnormal hemoglobin S and abnormal hemoglobin C (respectively H-V0, H-V1 and H-V2) can be identified by comparison with a chromatogram of a blood sample containing no such abnormal hemoglobin. Accordingly, when elution times at which H-V0, H-V1 and H-V2 appear under the predetermined conditions (in the case of examples in Figs., 1.0 minute, 1.2 minutes and 1.3 minutes, respectively) are stored, peaks derived from abnormal hemoglobin D, abnormal hemoglobin S and abnormal hemoglobin C can be identified from the elution times, so long as sA1c is measured under the same conditions.

EXAMPLES

Example 1

The method of the present invention was carried out such that in a chromatogram (FIG. 5) obtained by cation exchange chromatography with respect to a blood sample containing abnormal hemoglobin D, the total peak area (Total area) and the respective peak areas of A1a, A1b, HbF, LA1c, sA1c, A' and H-V0 were calculated, the X1c area was obtained from the formula (3), the A0 area was determined by the formula (2), and A1c % was calculated by the formula (1). The peak detection range for H-V0 was $1.00\pm0.07$ minutes.

(1) A' Peak Area
The A' peak area was calculated to be 921.2 from the chromatogram.
(2) $\alpha$ Peak Area
The $\alpha$ peak area was calculated to be 8.0+6.7+38.1+63.9=116.7 from the chromatogram.
(3) sA1c Peak Area
The sA1c peak area was calculated to be 63.9 from the chromatogram.
(4) X0 Peak Area
The X0=H-V0 peak area was calculated to be 576.7 from the chromatogram.
(5) $\beta$ Peak Area
The peak area can be calculated as Total area-HbF-$\alpha$-A'-X0, from the Total area, the $\beta$ peak area was calculated to be 1,645.2-12.6-116.7-921.2-576.7=18.0 from the chromatogram.
(6) Calculation of X1c
The above values were assigned to the formula (3) to calculate X1c=40.7.
(7) Calculation of A0
The above-obtained value of X1c was assigned to the formula (2) to calculate A0=880.5.
(8) Calculation of A1c %
The above-obtained values were assigned to the formula (1) to calculate A1c %=6.4%.
(9) Conversion to NGSP Units (Conversion Factors: 1.1151, 0.6558)

$$\text{NGSP converted value (\%)} = 6.4 \times 1.1151 + 0.6558 = 7.8 \text{ (\%)}$$

Example 2

The method of the present invention was carried out such that in a chromatogram (FIG. 6) obtained by cation exchange chromatography with respect to a blood sample containing abnormal hemoglobin S, the total peak area (Total area) and the respective peak areas of A1a, A1b, HbF, LA1c, sA1c, A' and H-V1 were calculated, the X1c area was obtained from the formula (3), the A0 area was determined by the formula (2), and A1c % was calculated by the formula (1). The peak detection range for H-V1 was $1.16\pm0.09$ minutes.

(1) A' Peak Area
The A' peak area was calculated to be 899.0 from the chromatogram.
(2) $\alpha$ Peak Area
The $\alpha$ peak area was calculated to be 11.8+7.8+31.4+78.6=129.6 from the chromatogram.
(3) sA1c Peak Area
The sA1c peak area was calculated to be 78.6 from the chromatogram.
(4) X0 Peak Area
The X0=H-V1 peak area was calculated to be 573.6 from the chromatogram.
(5) $\beta$ Peak Area
The peak area can be calculated as Total area-HbF-$\alpha$-A'-X0, from the Total area, the $\beta$ peak area was calculated to be 1,619.0-10.5-129.6-899.0-573.6=6.3 from the chromatogram.
(6) Calculation of X1c
The above values were assigned to the formula (3) to calculate X1c=50.7.
(7) Calculation of A0
The above-obtained value of X1c was assigned to the formula (2) to calculate A0=848.3.
(8) Calculation of A1c %
The above-obtained values were assigned to the formula (1) to calculate A1c %=8.0%.
(9) Conversion to NGSP Units (Conversion Factors: 1.1151, 0.6558)

$$\text{NGSP converted value (\%)} = 8.0 \times 1.1151 + 0.6558 = 9.6 \text{ (\%)}$$

Example 3

The method of the present invention was carried out such that in a chromatogram (FIG. 7) obtained by cation exchange chromatography with respect to a blood sample containing abnormal hemoglobin C, the respective peak areas of A1a, A1b, LA1c, sA1c and A0 were calculated, and A1c % was calculated by the formula (4). The peak detection range for H-V2 was $1.34\pm0.09$ minutes.

(1) A0 Peak Area
The A0 peak area was calculated to be 1,140.3 from the chromatogram.
(2) $\alpha$ Peak Area
The $\alpha$ peak area was calculated to be 10.8+11.8+34.8+89.9=147.3 from the chromatogram.

(3) sA1c Peak Area

The sA1c peak area was calculated to be 89.9 from the chromatogram.

(8) Calculation of A1c %

The above-obtained values were assigned to the formula (4) to calculate A1c %=6.7%.

(9) Conversion to NGSP Units (Conversion Factors: 1.1151, 0.6558)

NGSP converted value (%)=6.7×1.1151+0.6558=8.1 (%)

Example 4

Figure 8:
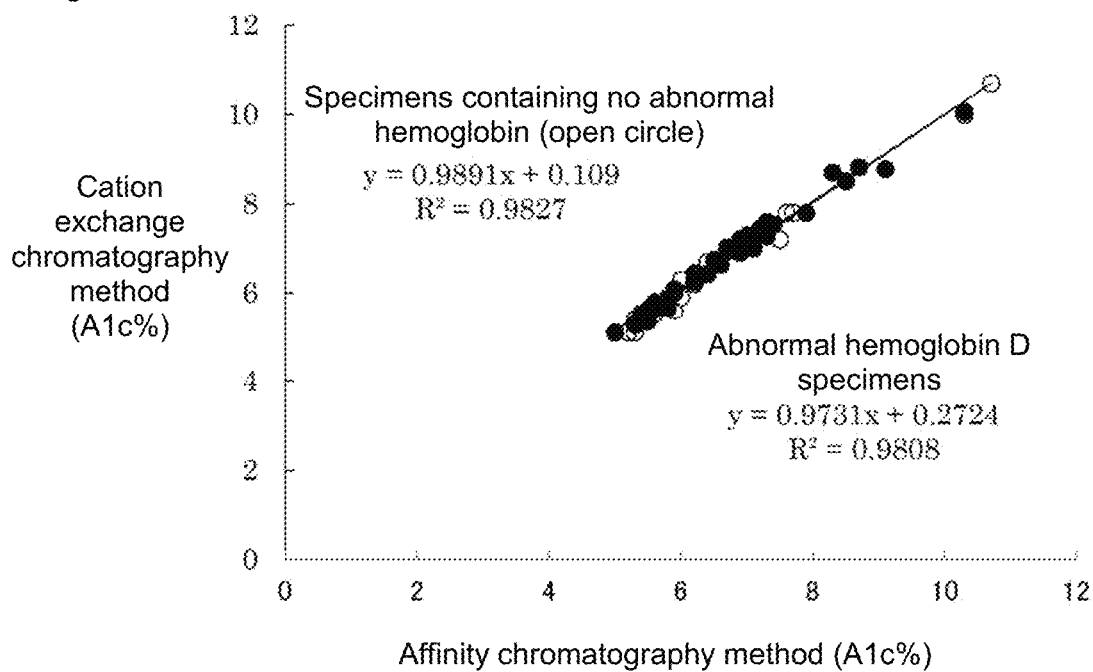
FIG. 8 is a diagram illustrating the correlation between measurement results by affinity chromatography and measurement results obtained by the method of the present invention by correcting A1c % based on the area of a remarkable peak (H-V0) corresponding to abnormal hemoglobin D and other peak area information on a chromatogram, with respect to blood samples containing abnormal hemoglobin D and blood samples containing no abnormal hemoglobin D.
Figure 9:
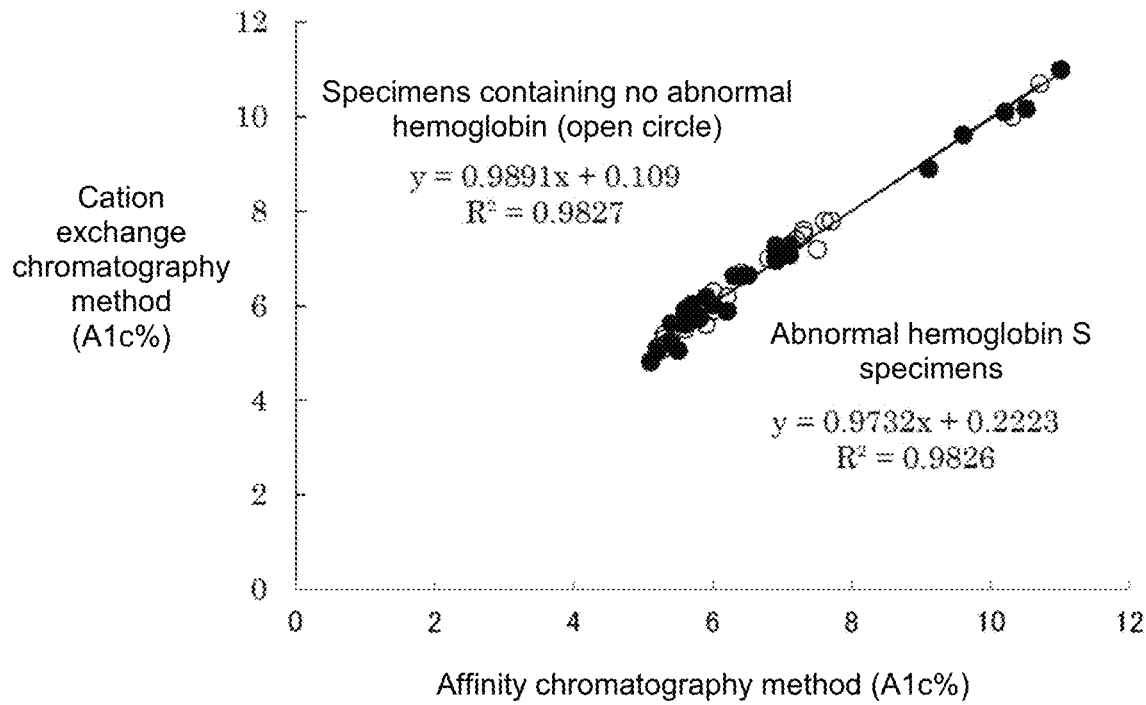
FIG. 9 is a diagram illustrating the correlation between measurement results by affinity chromatography and measurement results obtained by the method of the present invention by correcting A1c % based on the area of a remarkable peak (H-V1) corresponding to abnormal hemoglobin S and other peak area information on a chromatogram, with respect to blood samples containing abnormal hemoglobin S and blood samples containing no abnormal hemoglobin S.
Figure 10:
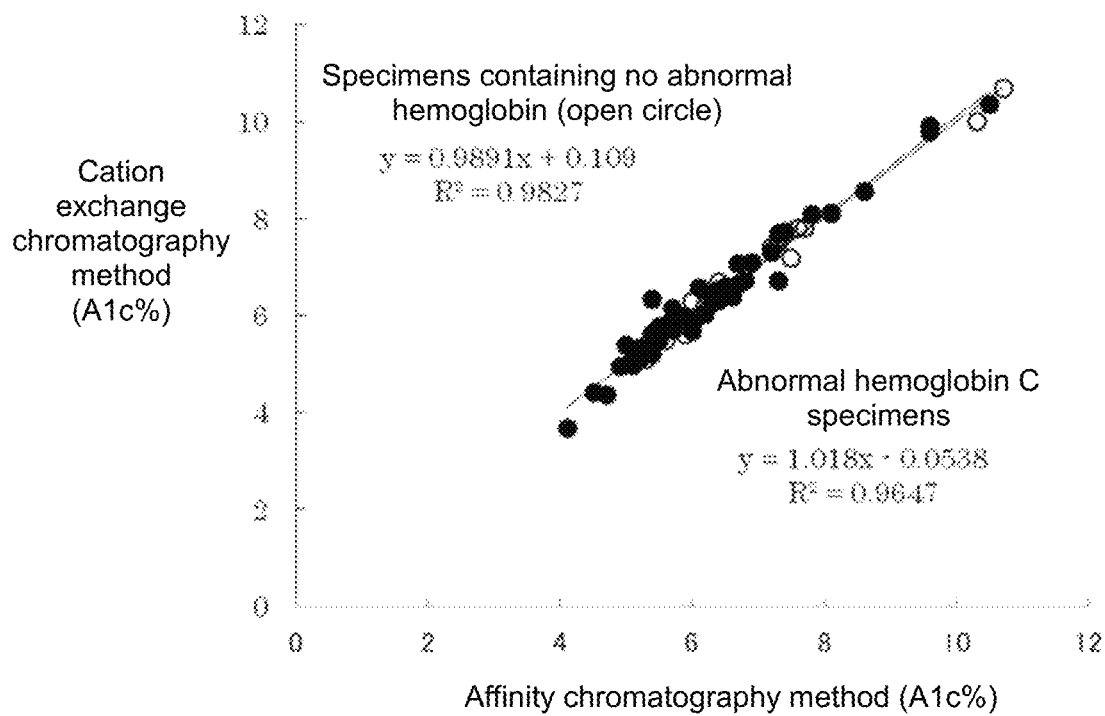
FIG. 10 is a diagram illustrating the correlation between measurement results by affinity chromatography and measurement results obtained by the method of the present invention by correcting A1c % based on the area of a remarkable peak (H-V2) corresponding to abnormal hemoglobin C and other peak area information on a chromatogram, with respect to blood samples containing abnormal hemoglobin C and blood samples containing no abnormal hemoglobin C.
Figure 11:
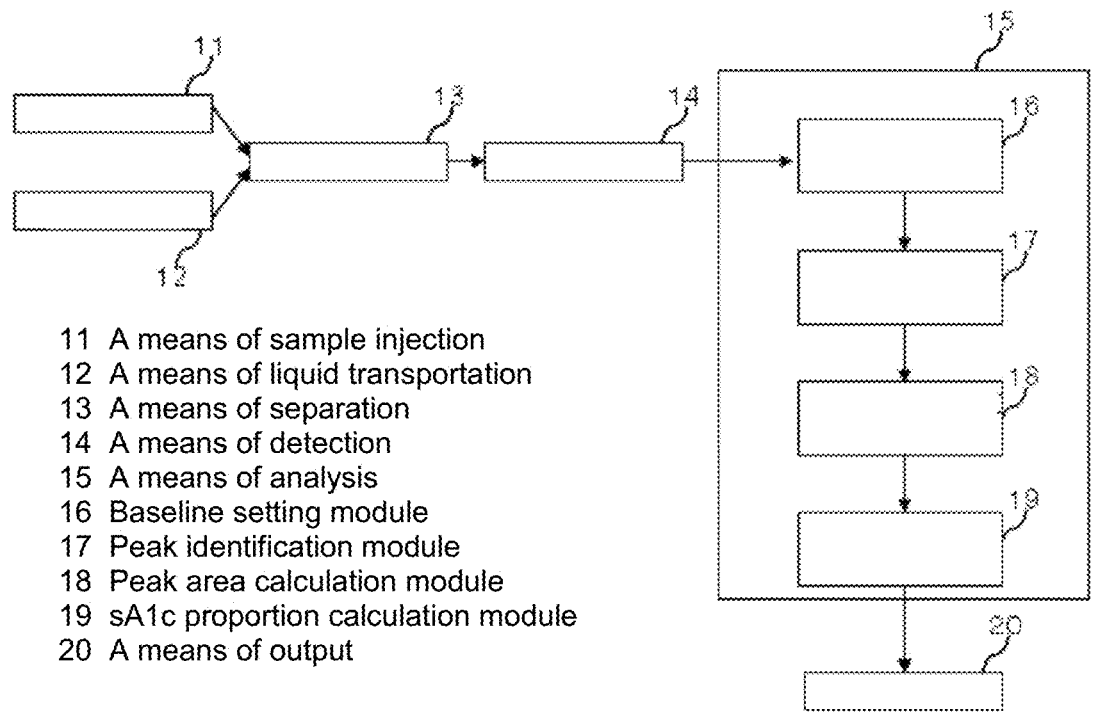
FIG. 11 is a diagram illustrating the measurement device of the present invention.
Figure 12:
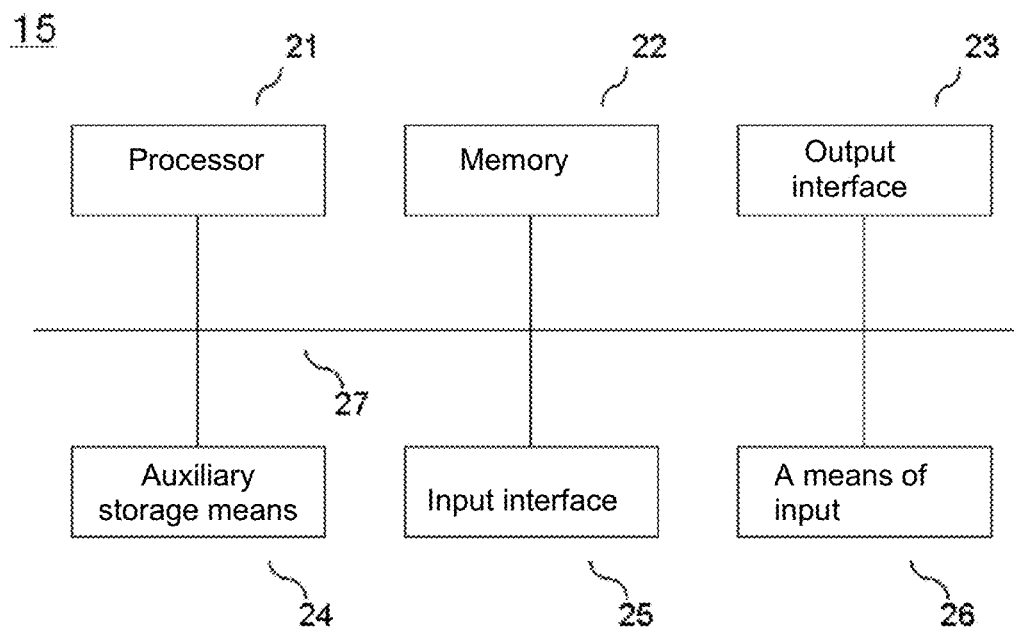
FIG. 12 is a diagram illustrating the measurement device of the present invention.

The present invention shown in Examples 1, 2 and 3 were applied to the chromatograms obtained by subjecting the blood samples containing abnormal hemoglobin D, S and C shown in FIGS. 5, 6 and 7 to cation exchange chromatography, and the results are shown in FIGS. 8, 9 and 10, respectively. As shown in these Figs., as a result of application of the present invention, the differences with measurement results by affinity chromatography are improved, and the slopes in the correlation coefficients were improved from 0.8841 to 0.9731, from 0.8767 to 0.9732, and from 0.8919 to 1.018, respectively as compared with FIGS. 1, 2, and 3.

The present invention was described in detail with reference to specific embodiments, however, it is obvious to those skilled in the art that various changes and modifications are possible without departing from the spirit and scope of the present invention.

The entire disclosure of Japanese Patent Application No. 2016-095191 filed on May 11, 2016 including specification, claims, drawings and summary is incorporated herein by reference in its entirety.

REFERENCE SYMBOLS

1 Cation exchange chromatography device
11 A means of sample injection
12 A means of liquid transportation
13 A means of separation
14 A means of detection
15 A means of analysis
16 Baseline setting module
17 Peak identification module
18 Peak area calculation module
19 sA1c proportion calculation module
20 A means of output

The invention claimed is:

1. A method for measuring stable glycated hemoglobin sA1c, which comprises (1) a step of subjecting a blood sample after hemolysis to cation exchange chromatography to elute sA1c as separated from other hemoglobin components thereby to obtain a chromatogram showing elution of hemoglobin fractions, (2) a step of identifying a sA1c peak in the obtained chromatogram and calculating its peak area, (3) a step of identifying peaks of hemoglobin components of hemoglobin A eluted before and including non-glycated peak of hemoglobin A, A0, other than sA1c in the obtained chromatogram and calculating their peak areas, (4) a step of calculating a proportion (%) of the sA1c peak area obtained in the step 2 to a total hemoglobin peak area which is a sum of the peak areas obtained in the step 3 and sA1c peak area obtained in the step 2, (5) a step of identifying a non-glycated peak of abnormal hemoglobin D, abnormal hemoglobin S or abnormal hemoglobin C from peaks which appear after the A0, and (6) a step of estimating an area of a glycated peak of abnormal hemoglobin D, abnormal hemoglobin S or abnormal hemoglobin C based on a non-glycated peak area of the abnormal hemoglobin identified, wherein the proportion (%) of the sA1c peak area in the above step 4 is corrected using the estimated glycated peak area of the identified abnormal hemoglobin, wherein when a non-glycated peak of abnormal hemoglobin D or abnormal hemoglobin S is identified in the step 5, the proportion (%) of the sA1c peak area to the total peak area of hemoglobin A is corrected in accordance with the following formulae, on an assumption that the glycated peak of the abnormal hemoglobin D or abnormal hemoglobin S appears as overlapping the A0, and that a proportion of the sA1c peak area to the total peak area of hemoglobin A is equal to a proportion of the glycated peak area of the abnormal hemoglobin to a sum of the peak areas of the glycated abnormal hemoglobin, non-glycated abnormal hemoglobin, and other peaks that elute after the A0 and do not include the peak of glycated abnormal hemoglobin and the peak of non-glycated abnormal hemoglobin:

$$A1c\ \% = 100 sA1c/(A0+\alpha) = 100 X1c/(X0+\beta+X1c)$$

$$A' = A0 + X1c$$

$$X1c = [(A'+\alpha-sA1c) - \sqrt{\{(A'+\alpha-sA1c)^2 - 4sA1c(X0+\beta)\}}]/2$$

wherein $A'$ is a sum of A0 and a glycated peak area of abnormal hemoglobin which coelutes with A0 and is an area of the peak observed as A0 on the chromatogram, sA1c and A0 are respectively glycated and non-glycated peak areas of hemoglobin A, X1c and X0 are respectively a glycated peak area of abnormal hemoglobin which coelutes with A0 and a non-glycated peak area of abnormal hemoglobin which appears after A0, $\alpha = A1a + A1b + LA1c + sA1c$, and $\beta$ is one obtained by subtracting X0 from a total area of peaks which appear after A0;

and when a non-glycated peak of abnormal hemoglobin C is identified in the step 5, the proportion (%) of the sA1c peak area to the total peak area of hemoglobin A is corrected in accordance with the following formula, on an assumption that the glycated peak of the abnormal hemoglobin C appears after the non-glycated peak A0 of hemoglobin A:

$$A1c\ \% = 100 sA1c/(A'+\alpha)$$

wherein $A'$ is a peak area observed as A0 on the chromatogram, sA1c and A0 are respectively glycated and non-glycated peak areas of hemoglobin A, and $$\alpha = A1a + A1b + LA1c + sA1c.$$

* * * * *